US00PP20260P2

(12) United States Plant Patent
Hooijman

(10) Patent No.: US PP20,260 P2
(45) Date of Patent: Sep. 1, 2009

(54) ***HYPERICUM* PLANT NAMED 'ESM KALUA'**

(50) Latin Name: *Hypericum androsaemum*
Varietal Denomination: Esm Kalua

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 15 days.

(21) Appl. No.: 11/998,808

(22) Filed: Nov. 30, 2007

(51) Int. Cl.
*A01H 5/00* (2006.01)

(52) U.S. Cl. ..... Plt./442
(58) Field of Classification Search ..... Plt./442, Plt./226
See application file for complete search history.

*Primary Examiner*—June Hwu
(74) *Attorney, Agent, or Firm*—C. A. Whealy

(57) ABSTRACT

A new and distinct cultivar of *Hypericum* plant named 'Esm Kalua', characterized by its upright, symmetrical and long flowering stems; moderately vigorous growth habit; dark green-colored leaves; uniform and freely flowering habit; uniform and high density of fruits; and large spherical greenish white-colored fruits.

2 Drawing Sheets

Botanical designation: *Hypericum androsaemum.*
Cultivar denomination: 'Esm Kalua'.

BACKGROUND OF THE INVENTION

The present invention relates to a new and distinct cultivar of *Hypericum,* botanically known as *Hypericum androsaemum* and hereinafter referred to by the name 'Esm Kalua'.

The new *Hypericum* is a product of a planned breeding program conducted by the Inventor in El Quinche, Pichincha, Ecuador. The objective of the breeding program is to create new *Hypericum* cultivars with numerous attractive fruits.

The new *Hypericum* originated from a cross-pollination in February, 2003 in El Quinche, Pichincha, Ecuador of a proprietary selection of *Hypericum androsaemum* identified as code designation Line 114, not patented, as the female, or seed parent with a proprietary selection of *Hypericum androsaemum* identified as code designation Line 56, not patented, as the male, or pollen, parent. The new *Hypericum* was discovered and selected by the Inventor as a single flowering plant within the progeny of the stated cross-pollination in a controlled environment in El Quinche, Pichincha, Ecuador.

Asexual reproduction of the new cultivar by vegetative cuttings in El Quinche, Pichincha, Ecuador, since August, 2003, has shown that the unique features of this new *Hypericum* are stable and reproduced true to type in successive generations.

SUMMARY OF THE INVENTION

Plants of the cultivar Esm Kalua have not been observed under all possible environmental conditions. The phenotype may vary somewhat with variations in environment such as temperature and light intensity without, however, any variance in genotype.

The following traits have been repeatedly observed and are determined to be the unique characteristics of 'Esm Kalua'. These characteristics in combination distinguish 'Esm Kalua' as a new and distinct cultivar of *Hypericum:*

1. Upright, symmetrical and long flowering stems.
2. Moderately vigorous growth habit.
3. Dark green-colored leaves.
4. Uniform and freely flowering habit; uniform and high density of fruits.
5. Large spherical greenish white-colored fruits.

Plants of the new *Hypericum* differ from plants of the female parent selection in the following characteristics:

1. Plants of the new *Hypericum* and the female parent selection differ in fruit color as plants of the female parent selection have green-colored fruits.
2. Plants of the new *Hypericum* are not as resistant to *Puccinia* rust as plants of the female parent selection.

Plants of the new *Hypericum* differ from plants of the male parent selection in the following characteristics:

1. Plants of the new *Hypericum* are not as vigorous as plants of the male parent selection.
2. Plants of the new *Hypericum* are more freely flowering than plants of the male parent selection.
3. Plants of the new *Hypericum* have spherical-shaped fruits whereas plants of the male parent selection have elliptical-shaped fruits.
4. Plants of the new *Hypericum* and the male parent selection differ in fruit color as plants of the male parent selection have orange-colored fruits.

Plants of the new *Hypericum* can be compared to plants of the cultivar Esm Bonaire, not patented. In side-by-side comparisons conducted by the Inventor in El Quinche, Pichincha, Ecuador, plants of the new *Hypericum* differed from plants of the cultivar Esm Bonaire in the following characteristics:

1. Plants of the new *Hypericum* were broader and had shorter internodes than plants of the cultivar Esm Bonaire.
2. Plants of the new *Hypericum* had larger inflorescences than plants of the cultivar Esm Bonaire.

3. Plants of the new *Hypericum* flowered later than plants of the cultivar Esm Bonaire.
4. Plants of the new *Hypericum* were more freely flowering than plants of the cultivar Esm Bonaire.
5. Plants of the new *Hypericum* had larger flowers than plants of the cultivar Esm Bonaire.
6. Plants of the new *Hypericum* had larger fruits than plants of the cultivar Esm Bonaire.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Hypericum*.

The photograph on the first sheet is a side perspective view of typical flowering plants of 'Esm Kalua'.

The photograph at the top of the second sheet comprises a side perspective view of a typical stem of 'Esm Kalua' with mature fruits.

The photograph at the bottom of the second sheet is a close-up view of a typical fruit of 'Esm Kalua'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions in an outdoor nursery in El Quinche, Pichincha, Ecuador for about one year. During the production of the plants, day temperatures ranged from 12° C. to 30° C., night temperatures ranged from 5° C. to averaged 12° C. and light levels ranged from 1,000 to 1,150 foot-candles.

Botanical classification: *Hypericum androsaemum* cultivar Esm Kalua.

Parentage:

*Female, or seed, parent.*—Proprietary selection of *Hypericum androsaemum* identified as code designation Line 114, not patented.

*Male, or pollen, parent.*—Proprietary selection of *Hypericum androsaemum* identified as code designation Line 56, not patented.

Propagation:

*Type cutting.*—Vegetative cuttings.

*Time to initiate roots.*—About seven to ten days at 22° C. to 30° C.

*Time to produce a rooted young plant.*—About four to five weeks at 22° C. to 30° C.

*Root description.*—Fine, fibrous; between 165B and 200C in color.

*Rooting habit.*—Freely branching; moderately dense.

Plant description:

*Form.*—Typically grown as a cut flower-type *Hypericum*. Upright, symmetrical and long flowering stems; moderately vigorous growth habit; basally branching habit with about four to five flowering stems developing per plant per year.

*Plant height.*—About 100 cm.

*Plant width* (*spread*).—About 42 cm.

*Lateral branch description.*—Length: About 96 cm. Diameter: About 5 mm. Internode length: About 4.7 cm. Strength: Strong. Texture: Smooth, glabrous. Color: 145C overlain with 174B.

Foliage description:

*Arrangement.*—Opposite, simple; sessile.

*Length.*—About 7 cm.

*Width.*—About 4.2 cm.

*Shape.*—Ovate.

*Apex.*—Obtuse to retuse.

*Base.*—Truncate to slightly cordate.

*Margin.*—Entire.

*Texture, upper and lower surfaces.*—Smooth, glabrous; papery.

*Venation pattern.*—Pinnate.

*Color.*—Developing foliage, upper surface: Close to 137A. Developing foliage, lower surface: Close to 146B. Fully expanded foliage, upper surface: Close to 137A; venation, close to 144C. Fully expanded foliage, lower surface: Close to 138A; venation, 148C.

Flower description:

*Flower arrangement and shape.*—Bright yellow-colored single flowers arranged in terminal compound umbels; freely flowering habit with about twelve flowers per umbel. Flowers not persistent. Flowers face mostly upright.

*Fragrance.*—Moderate.

*Natural flowering season.*—Year-round in Ecuador.

*Flower longevity.*—Flowers last about two to four days on the plant. Flowers not persistent.

*Flower buds.*—Length: About 5 mm. Diameter: About 6 mm. Shape: Globose. Color: 15A.

*Inflorescence size.*—Length: About 14 cm. Diameter: About 17 cm.

*Flowers.*—Diameter: About 2.8 cm. Depth (height): About 1.3 cm.

*Petals.*—Quantity/arrangement: Five in a single whorl. Length: About 1.5 cm. Width: About 1 cm. Shape: Oval. Apex: Obtuse. Base: Attenuate. Margin: Entire. Texture, upper and lower surfaces: Glabrous, smooth; papery. Aspect: Incurved; concave. Color: When opening, upper surface: 14B. When opening, lower surface: 13B. Fully opened, upper surface: 14A; color becoming lighter than 14A with development. Fully opened, lower surface: 14B.

*Sepals.*—Quantity/arrangement: Five in a single whorl; three larger than the other two. Length: About 9 mm to 12 mm. Width: About 5 mm to 8 mm. Shape: Ovate to round. Apex: Obtuse. Base: Attenuate. Margin: Entire. Texture, upper and lower surfaces: Glabrous, smooth. Color: When opening, upper surface: Close to 143B. When opening, lower surface: Close to 139C. Fully opened, upper surface: Close to 143B. Fully opened, lower surface: Close to 145B.

*Peduncles.*—Strength: Strong. Length: About 4.8 cm. Diameter: About 2 mm. Texture: Smooth, glabrous. Color: 174B overlain with 145C.

*Pedicels.*—Strength: Strong. Length: About 1.4 cm. Diameter: About 2 mm. Aspect: About 40° from the stem axis. Texture: Smooth, glabrous. Color: 144B.

*Reproductive organs.*—Stamens: Quantity per flower: About 100. Anther shape: Reniform. Anther length: About 1 mm. Anther color: Close to 15A. Pollen amount: Abundant. Pollen color: Close to 13A. Pistils: Quantity per flower: Single pistil with three stigmas. Pistil length: About 1.1 cm. Stigma shape: Circular. Stigma color: Close to 181C. Style length: About 4 mm. Style color: Close to 1B. Ovary color: Close to 154B.

*Fruits.*—Length: About 1.1 cm. Diameter: About 1.2 cm. Shape: Roughly spherical. Texture: Smooth, glabrous. Color: Between 10C and 150D; towards the base, close to 155D.

*Seeds.*—Length: About 0.1 mm. Diameter: About 0.03 mm. Color: Close to 200C.

Disease/pest resistance: Plants of the new *Hypericum* have not been noted to be resistant to pathogens and pests common to *Hypericum.*

Weather/temperature tolerance: Plants of the new *Hypericum* have been observed to tolerate wind, rain and temperatures ranging from about 0° C. to about 35° C.

It is claimed:

1. A new and distinct *Hypericum* plant named 'Esm Kalua' as illustrated and described.

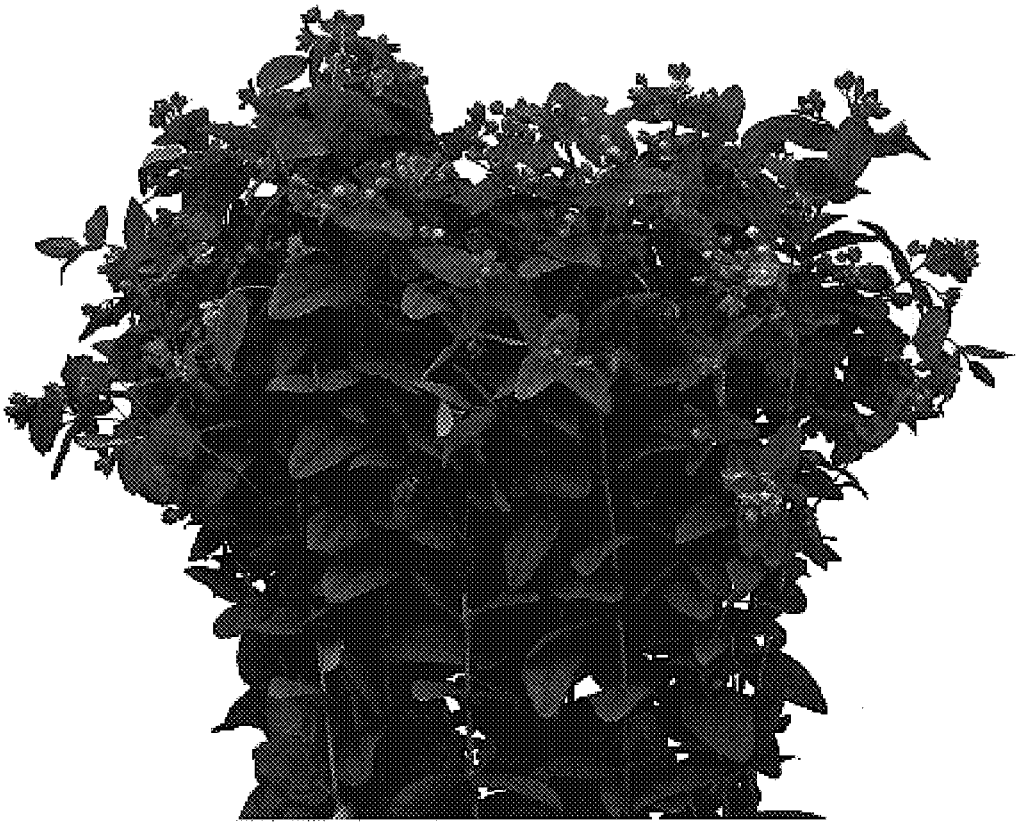

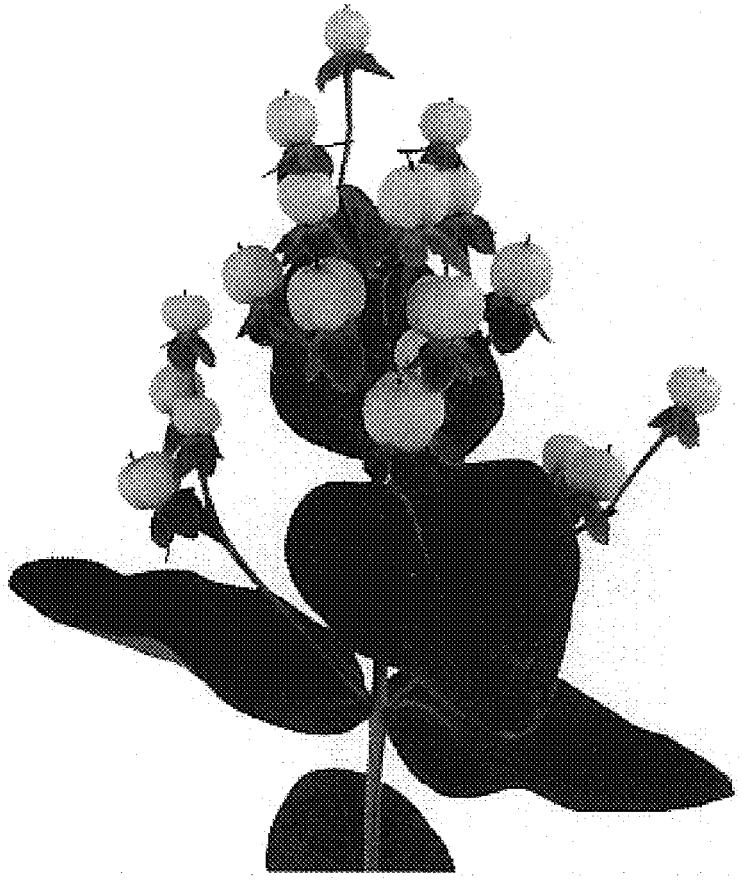
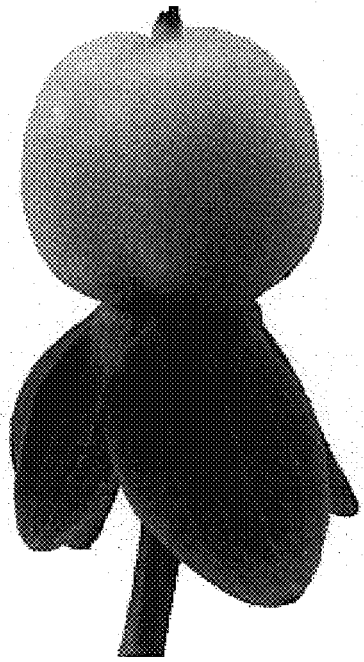

* * * * *